United States Patent [19]

Schoennauer et al.

[11] Patent Number: 4,850,697
[45] Date of Patent: Jul. 25, 1989

[54] RESONANT PIEZOELECTRIC CHOPPER FOR INFRARED RADIATION

[75] Inventors: Larry J. Schoennauer; Ronald B. Alers; Keith Kaste; Ross E. Johnson, all of San Luis Obispo; Jacob Y. Wong, Santa Barbara, all of Calif.

[73] Assignee: Dynatech Electro-Optics Corporation, San Luis Obispo, Calif.

[21] Appl. No.: 168,966

[22] Filed: Mar. 16, 1988

[51] Int. Cl.[4] .............................................. G01J 3/51
[52] U.S. Cl. .................................... 356/419; 250/339; 250/351; 350/315; 350/318
[58] Field of Search .......................... 356/416, 419, 51; 350/315, 317, 318, 387, 266; 250/339, 351

[56] References Cited

U.S. PATENT DOCUMENTS 4,485,305 11/1984 Kuwano et al. ..................... 250/351
4,599,001 7/1986 Richard ................................ 350/318
4,631,406 12/1986 Nakata ................................. 250/351

Primary Examiner—F. L. Evans
Attorney, Agent, or Firm—Daniel C. McKown

[57] ABSTRACT

Apparatus for inserting and removing several filters from an optical path and for determining at all times the instantaneous positional relationship of each filter with respect to the optical path includes a set of filters mounted on a carrier which is attached to a resonant piezoelectric system, and further includes reference tracks also located on the carrier and extending in the direction of the oscillatory motion and including a sequence of binary indicia progressing in the direction of the oscillatory motion. The reference tracks are read optically to produce a series of binary electrical signals which are processed to yield the instantaneous position of the carrier and filters with respect to a fixed optical path.

10 Claims, 2 Drawing Sheets

RESONANT PIEZOELECTRIC CHOPPER FOR INFRARED RADIATION

BACKGROUND OF THE INVENTION

1. Field of the Invention

The present invention is in the field of infrared radiation and specifically relates to a device for physically interposing a number of filters into a beam of infrared radiation in a fixed sequence.

2. The Prior Art

The device of the present invention is expected to find its greatest application in nondispersive infrared gas analyzers in which the presence of particular gas components is tested by interposing several infrared radiation filters in a beam of infrared radiation. In a typical instrument, the filters have narrow bandpasses which are centered at absorption lines that are characteristic of the various components.

Because the characterizing absorption lines lie in the infrared portion of the electromagnetic spectrum, there is a likelihood that the results might be distorted by background infrared radiation emitted from surrounding objects at room temperature.

Fortunately, the background radiation is emitted continuously, which suggests that modulation of the test beam can be used to distinguish its radiation from the continuous radiation of the background.

Where only a single wavelength is involved, the use of spoked chopper wheels is well known. These wheels consist of alternating opaque and transparent areas, and are usually driven by an electrical motor. It is also known to put filters in the openings in the chopper wheel where multiple wavelength operation is desired. Motor-driven wheels have some disadvantages, such as the size and weight of the motor, power consumption, bearing wear, and mechanical vibration. It is also known that some of these disadvantages can be overcome by mounting the optical filters on a tuning fork or other structure driven at resonance by an electromagnet.

The vibrating devices are not without disadvantages. For example, the midpoint of the oscillation depends on the orientation of the apparatus with respect to gravity. Likewise, any acceleration experienced by the device will have a similar effect. Further, vibrating devices do not provide a constant linear velocity. Finally, if because of fluctuations in the driving current or variations in temperature, the amplitude of the vibration does not remain constant, the operation of the system could be impaired. Although the device of the present invention falls into the class of resonating instruments, the present invention includes means that prevent these problems from arising.

Certain aspects of the present invention are shown in the prior art, as disclosed below. However, it appears that the specific combination of features advantageously employed in the present invention is truly novel.

In U.S. Pat. No. 3,694,086, May shows the use of a piezoelectric transducer to selectively and cyclically introduce filters into an optical path. The filters are mounted on the end of a piezo crystal transducer, which lengthens and shortens in response to applied electrical signals. The device does not make use of mechanical resonance, and the amplitude of the vibration must be relatively small.

In U.S. Pat. No. 3,135,869, Rosenthal shows a mirror mount that employs a non-resonant piezoelectric mechanism for tilting a mirror about two orthogonal axes.

In U.S. Pat. No. 4,171,918, Mactaggart shows a tuning fork driven at resonance by an electromagnet for alternately introducing two filters of different wavelengths into the optical path. A similar system is shown by Dewey, Jr. in U.S. Pat. No. 3,853,407.

In U.S. Pat. No. 3,020,414, McKnight, et al. show a mirror scanning mechanism that employs electromagnets to tilt a torsionally-mounted mirror. In U.S. Pat. No. 3,071,036 McKnight, et al. show the use of five electromagnets to produce nutation of a mirror by sequential activation of the driving coils.

In U.S. Pat. No. 3,877,812, Thompson shows a clockwork type of device that uses a cam to generate the motion that changes from one filter to the next.

In U.S. Pat. No. 3,529,889, De Mey II shows a motor-driven non-resonant mechanism for sliding a desired filter into position.

In U.S. Pat. No. 3,194,962, Carlon, et al. show a filter wheel driven by an electric motor.

In U.S. Pat. No. 4,264,209, Brewster shows an electromagnetically driven pendulum on which are mounted two filters.

As will be seen below, the device of the present invention overcomes certain problems that were inherent in these prior art inventions to achieve a new and useful result.

SUMMARY OF THE INVENTION

In one aspect, the present invention provides the advantages of a filter wheel that is driven by a motor at a constant speed in a device in which the filters move with variable linear speed.

In another aspect, the present invention provides low power consumption, typical of resonant systems, but unlike other resonant systems, the present invention is indifferent to acceleration.

In accordance with the present invention, an array of filters is mounted on a carrier which is attached to the free end of a cantilevered resilient beam. A sheet of piezoelectric material is bonded to each side of the cantilevered beam, and a thin layer of a conductive material is applied on the exposed face of each sheet of piezoelectric material. The conductive layers are connected to a source of voltage pulses of alternating polarity. When a voltage is applied to the electrodes, the composite structure bends in a direction determined by the polarity of the voltage. The alternating voltage causes the composite structure to bend in alternating directions, thereby causing alternating movement of the carrier and its filters, so that any radiation passing along the optical path will fall on the various filters as they are moved through the optical path.

In addition to the filters, the carrier also includes at least one reference track that includes a sequence of binary indicia progressing in the direction of the oscillating motion. The presence of these indicia is sensed by a separate beam of radiation in the preferred embodiment for the purpose of determining the instantaneous position of the carrier and filters at each point in a cycle of the oscillating motion.

It is important to note that the reference track is not used merely for generating a sync signal for synchronizing the operation of an associated detector, but in addition, the reference track permits the instantaneous position of each filter to be determined at all times throughout the cycle of oscillation.

In the preferred embodiment, two reference tracks are used. The first signals the beginning of a scan, while the second consists of a number of relatively finely spaced lines which are counted, for determining the instantaneous position of the filters within the scan.

In a first alternative embodiment, the reference tracks permit the determination of which filter is in the optical path at a particular instant through the use of a binary coding scheme.

In a second alternative embodiment, the instantaneous position of the carrier is converted to a digital signal.

The novel features which are believed to be characteristics of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
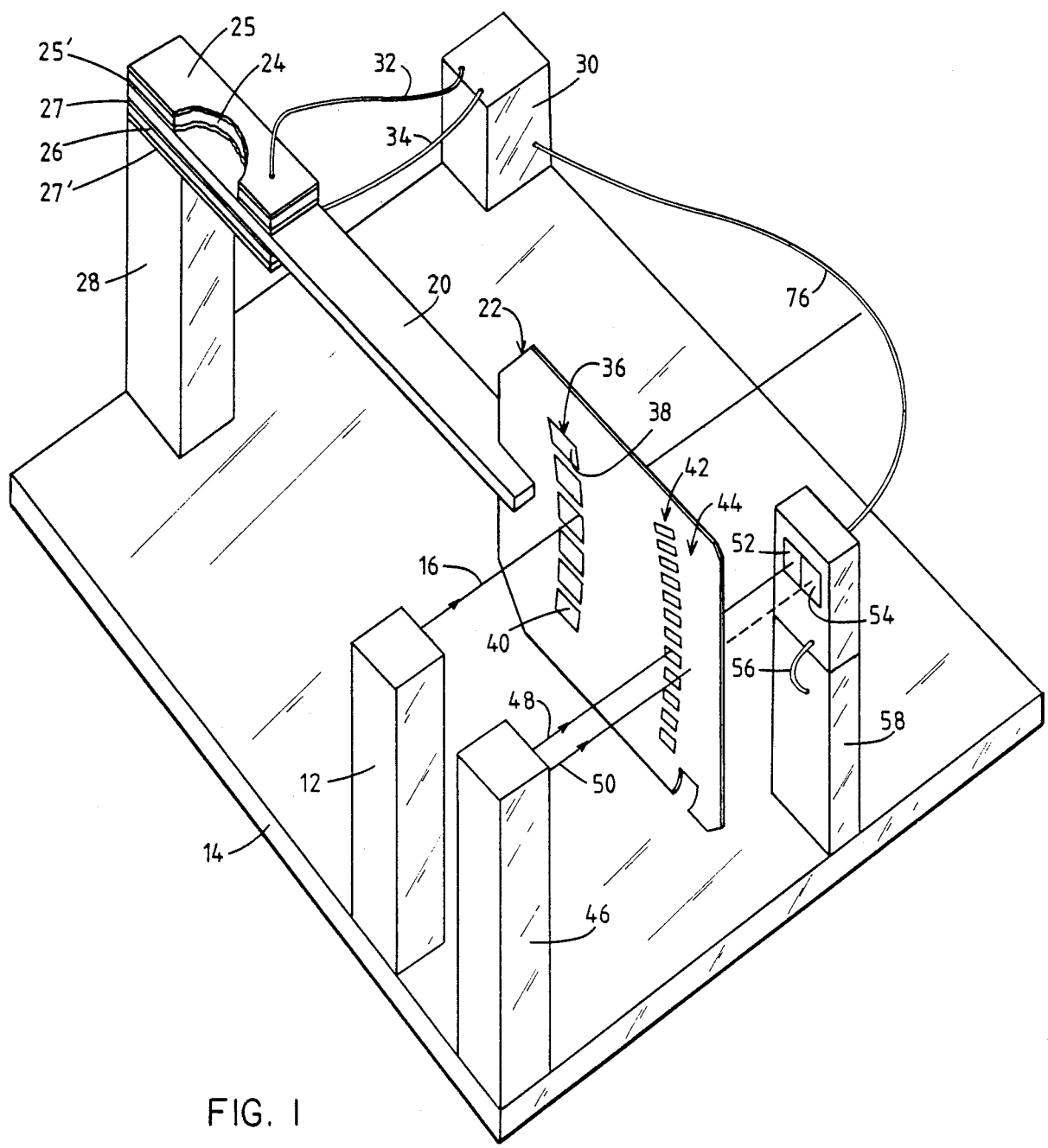
FIG. 1 is a perspectiveive view showing a preferred embodiment of the invention.

The apparatus of the present invention can be used in association with various kinds of optical equipment. The apparatus of the present invention permits a number of filters to be placed in an optical path, which is the path taken by radiation produced by the associated optical equipment.

For purposes of this description, the word optical is defined to include infrared radiation and ultraviolet radiation in addition to visible radiation. As explained above, the use of a chopper is particularly helpful when infrared radiation is used.

For purpose of the present description, the radiation travelling in the direction indicated on the optical path 16 originates in a radiation source 12 that is connected to the base 14. The optical path 16 is not a material object, but is a line indicating the direction that the radiation is travelling. The optical path 16 remains fixed with respect to the base 14.

The base 14 includes a support 28, from which a cantilevered beam 20 extends. A carrier 22 is attached to the free end of the cantilevered beam.

The cantilevered beam 20 is composed of an insulative material. In the preferred embodiment it is MYLAR®.

Thin conductive layers 25, 25' and 27, 27' are applied to the faces of plates 24, 26 of a piezoelectric material, respectively to serve as electrodes. Thereafter, the plates are bonded to opposite sides of the cantilevered beam 20 to form the structure shown in FIG. 1. In the preferred embodiment, the layers 25' and 27 are electrically connected to each other and to the wire 34, and likewise, the layers 25 and 27' are connected to each other and to the wire 32. In the preferred embodiment the piezoelectric material is lithium tantalate. The wires 32, 34 are bonded to the thin layers 25, 27 of conductive material. The wires 32, 34 are connected to a source 30 of voltage pulses, and the thin layers 25, 27 of conductive material insure that the voltage is applied uniformly over the plates 24, 26. The source 30 preferably produces pulses of alternating polarity, and in the preferred embodiment the source 30 produces a sinusoidal voltage, referred to as the excitation voltage.

Application of the excitation voltage causes the cantilevered beam 20 to deflect upwardly and downwardly in succession, so that the carrier 22 moves up and down in an oscillatory motion, as viewed in FIG. 1.

It can be appreciated that the mechanical system consisting of the carrier 22, and the cantilevered beam 20 has a resonant frequency dependent upon the stiffness of the beam 20 and the mass of the moving parts. The manner in which the voltage pulses on the wires 32, 34 are generated in phase with the oscillating motion of the cantilevered beam 20 and carrier 22 will be described in greater detail below.

The carrier 22 serves to hold the row 36 of filters 38 through 40. In addition, in accordance with the present invention, the carrier 22 further includes at least one reference track, of which the reference tracks 42, 44 of FIG. 1 are typical.

The term "filter" is used broadly herein, and includes, without limitation, narrow band, broad band, absorption filters, bandpass filters, and even totally opaque areas and totally transmissive areas. The opaque area could be formed by the occluding surface of the carrier 22, and the totally transmissive areas could consist of a hole through the carrier 22. If transparent and opaque areas alternate along the row 36, the row 36 would, in conventional usage, be called a chopper, and such devices are within the scope of the present invention.

In accordance with the present invention, the individual filters in the row 36 may have different widths in the direction of the oscillatory motion. In one embodiment of the present invention, the widths of the filters nearer the ends of the row 36 are of diminished length, to compensate for the changing linear velocity of the carrier during its oscillatory motion, so as to achieve an approximately constant dwell time on each individual filter.

In accordance with the present invention, the nature of the radiation source 12 is of no consequence, so long as it produces a beam of radiation that moves along the optical path 16.

Probably the most distinctive feature of the present invention is the provision of one or more reference tracks on the carrier 22. These tracks permit the instantaneous position of the carrier 22 with respect to the optical path 16 to be determined at all points in each cycle of the oscillatory motion.

This aspect of the present invention goes a major step beyond the use of a synchronizing pulse generated at an identifiable point within each cycle. When a single synchronizing pulse is used, it is necessary to assume that the motion of the chopper during the remainder of the cycle is predictable; i.e., sinusoidal or, in the case of a rotating wheel, of uniform velocity. If environmental factors, e.g., unexpected acceleration, invalidate this assumption, the use of a synchronizing pulse as a basis for establishing the timing of certain events during the scanning cycle will yield incorrect results. In this sense, systems using a synchronizing pulse are accurate only at one point in each cycle, whereas, in contrast, the system of the present invention gives the location of each filter accurately at all times during a scan cycle.

In a preferred embodiment of the present invention, information is derived from the reference tracks 42, 44 by an optical technique. It is recognized that in another embodiment, a magnetic or capacitive technique could be used. For example, the reference tracks could be strips of prerecorded magnetic tape that are affixed to the carrier 22 and that would be read by juxtaposing a magnetic playback head against the strip of recorded magnetic tape.

In the preferred embodiment, positional information is derived from the reference tracks 42, 44 by use of a light source 46 that produces beams of light that travel along the optical paths 48, 50 to examine the reference tracks 42, 44, respectively.

In accordance with a preferred embodiment of the invention, the reference tracks 42, 44 include a plurality of binary indicia that modulate the light travelling on the optical paths 48, 50. In the preferred embodiment shown in FIG. 1, the binary indicia consist of holes and solid portions in the carrier 22. In another embodiment, the indicia could include areas of high and low reflectivity. Also, it is recognized that the wavelength of the light generated by the light source 46 does not have to be the same as the wavelength of the radiation on the path 16.

In the preferred embodiment, the light on the optical paths 48, 50 falls on the detectors 52, 54 which convert the light into electrical signals representative of the binary indicia. These electrical signals are then carried by the cable 56 to a readout which is responsive to the electrical signals to produce electrical outputs representative of the instantaneous position of each filter with respect to the optical path 16.

Figure 2:
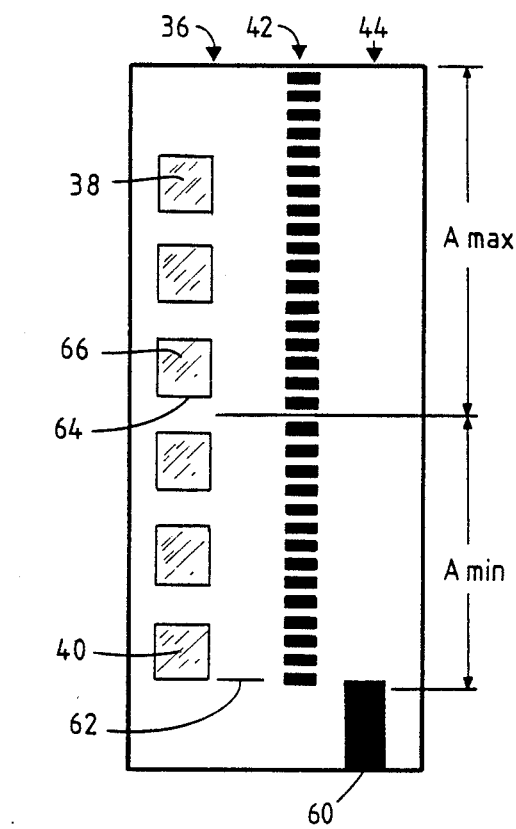
FIG. 2 is a diagram showing the layout of the filters and reference tracks in the preferred embodiment.

The reference tracks 42, 44 of FIG. 1 are shown in the diagram of FIG. 2 for greater clarity. The reference track 42 consists of an alternating sequence of holes and solid areas. In the diagram of FIG. 2, the holes are represented by the dark areas. Although a relatively small number of holes are shown in FIG. 2, for ease of illustration, in the preferred embodiment a much larger number of holes is used.

As shown in FIG. 2, the reference track 44 consists of a single hole 60 located at an extremity of the oscillatory motion. So long as the amplitude of the oscillatory motion is between $A_{min}$ and $A_{max}$, the hole 60 will produce a single pulse that indicates upon its termination that the beam on the path 48 is about to begin its passage along the reference track 42 (upwardly as viewed in FIG. 2). In the preferred embodiment, the pulse generated by the hole 60 is used to reset a digital decoder, and the pulses generated from the reference track 42 are used to increment the digital decoder, which then can be used to apply the output of a detector in the optical path 16 to an appropriate terminal on the basis of which filter is in the path at a particular instant.

Figure 3:
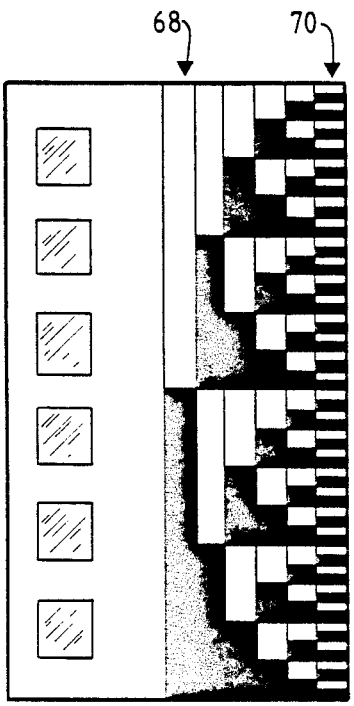
FIG. 3 is a diagram showing the layout of the filters and reference tracks in a first alternative embodiment; and, FIG. 4 is a diagram showing the layout of the filters and reference tracks in a second alternative embodiment.

In an alternative embodiment suitable for use with any amplitude of oscillatory motion and shown in FIG. 3, six reference tracks 68 through 70 are used. These tracks correspond to successive binary digits in a binary number that represents the position in the direction of the oscillation.

Figure 4:
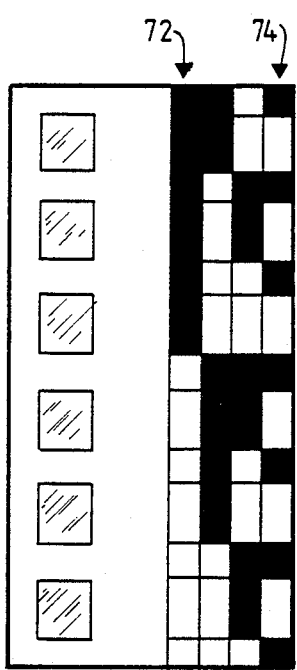

In some applications, it is only necessary to know which one of the filters the optical path 16 is passing through. In this case, the scheme shown in FIG. 4 can be used. The filters and the spaces adjacent them are assigned binary numbers, and four tracks 72 through 74 are used in the example of FIG. 4 which employs six filters. Note that the digits in the track 74 indicate whether a filter or an opaque adjacent area is in the optical path 16.

Returning now to the manner in which the source 30 of voltage impulses drives the piezoelectric chopper of the present invention, the technique used is as follows. When the apparatus is first turned on, the source 30 generates a sinusoidal excitation voltage at a frequency corresponding approximately to the resonant frequency of the carrier 22 and its support structure. The initial driving frequency corresponds to the resonant frequency measured under standard conditions. This initial excitation is adequate to bring the system into oscillation. However, because the environmental conditions that prevail may be different from the standard conditions, it is likely that the driving frequency will not be identical to the prevailing actual resonant frequency. Over a relatively long time, this very small discrepancy could result in an accumulated phase difference such that at some later time, the energizing impulses would be applied at exactly the wrong time. In any event, a severe decrease in amplitude would be observed unless some provision were made to relate the frequency of the driving voltage impulses to the actual resonant frequency.

In accordance with the present invention, this is accomplished by monitoring the timing and duration of the pulse generated by the hole 60 in the reference track 44 of the preferred embodiment shown in FIG. 2. It is recognized that if the driving frequency coincides exactly with the prevailing resonant frequency, a maximum amplitude will be achieved, and the width of the pulse generated by the hole 60 will be constant.

If the driving frequency departs from the prevailing resonant frequency, the amplitude of the oscillation necessarily diminishes.

The pulse detected by the detector 54 is converted to an electrical signal which is applied via the wire 76 to the source 30, which monitors the duration and timing of the detected pulse to correct the driving frequency.

Thus, there has been described apparatus for inserting and removing at least one filter from an optical path and for producing a signal that represents the instantaneous positional relationship of the filter with respect to the optical path.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. Apparatus for inserting and removing at least one filter from an optical path and for producing a signal that represents the instantaneous positional relationship of the filter with respect to the optical path, said apparatus comprising:
   a base;
   optical means connected to said base and defining an optical path that is fixed with respect to said base;
   a carrier;

a source of excitation voltage;

piezoelectric means for resiliently mounting said carrier to said base, connected to said source of excitation voltage and responsive to said excitation voltage for driving said carrier in an oscillatory motion with respect to said base;

filter means so located on said carrier as to pass into and out of the optical path during the oscillatory motion;

a reference track located on said carrier, extending in the direction of the oscillatory motion, and including a sequence of indicia progressing in the direction of the oscillatory motion;

pickoff means mounted on said base for sensing the indicia of said reference track during the oscillatory motion and for producing an electrical signal representative of the indicia; and, readout means electrically connected to said pick-off means and responsive to said electrical signal to produce an electrical output representative of the instantaneous positional relationship of said filter means with respect to the optical path.

2. The apparatus of claim 1 wherein said source of excitation voltage generates voltage pulses at a frequency approximately equal to the resonant frequency of said carrier.

3. The apparatus of claim 2 wherein said source of excitation voltage generates a sinusoidal voltage at a frequency approximately equal to the resonant frequency of said carrier.

4. The apparatus of claim 1 wherein said piezoelectric means further include an electrically insulative cantilevered beam having two opposite sides, and further includes a plate of piezoelectric material bonded to each of said two opposite sides.

5. The apparatus of claim 1 wherein said filter means further comprise an optically opaque substance.

6. The apparatus of claim 1 wherein said filter means further comprise an optically transparent area.

7. The apparatus of claim 1 wherein said reference track further includes optically transparent and optically opaque areas alternating in the direction of the oscillatory motion.

8. The apparatus of claim 7 wherein the indicia change at spaced intervals along the reference track.

9. The apparatus of claim 7 wherein the indicia correspond N-to-one to the more than one filters, where N is an integer greater than 1.

10. The apparatus of claim 1 wherein said pickoff means further include optical sensing means.

* * * * *